(12) United States Patent
Khairkhahan

(10) Patent No.: US 7,762,943 B2
(45) Date of Patent: Jul. 27, 2010

(54) INFLATABLE VENTRICULAR PARTITIONING DEVICE

(75) Inventor: Alexander Khairkhahan, Palo Alto, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 0 days.

(21) Appl. No.: 10/791,916

(22) Filed: Mar. 3, 2004

(65) Prior Publication Data

US 2005/0197716 A1 Sep. 8, 2005

(51) Int. Cl.
*A61F 2/00* (2006.01)
*A61F 13/00* (2006.01)
*A61F 2/04* (2006.01)
*A61N 1/362* (2006.01)
*A61M 29/00* (2006.01)

(52) U.S. Cl. .................. 600/37; 600/16; 623/23.67; 606/191

(58) Field of Classification Search .............. 623/23.67; 606/200, 213, 153, 16, 37, 198, 191, 192; 600/16, 17, 37
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,425,908 A * | 1/1984 | Simon | 128/899 |
| 4,619,246 A | 10/1986 | Molgaard-Nielsen et al. | |
| 4,685,446 A * | 8/1987 | Choy | 600/18 |
| 4,710,192 A | 12/1987 | Liotta et al. | |
| 4,832,055 A | 5/1989 | Palestrant | |
| 4,917,089 A | 4/1990 | Sideris | |
| 5,104,399 A | 4/1992 | Lazarus | |
| 5,192,301 A | 3/1993 | Kamiya et al. | |
| 5,192,314 A * | 3/1993 | Daskalakis | 623/3.21 |
| 5,375,612 A | 12/1994 | Cottenceau et al. | |
| 5,385,156 A | 1/1995 | Oliva | |
| 5,425,744 A | 6/1995 | Fagan et al. | |

(Continued)

FOREIGN PATENT DOCUMENTS

WO    WO 00/27292    5/2000

(Continued)

OTHER PUBLICATIONS

Tetsuji Kawata et al., "Systolic and Diastolic Function After Patch Reconstruction of Left Ventricular Aneurysms", Ann. Thorac. Surg. 59, pp. 403-407, 1995.

(Continued)

*Primary Examiner*—Alvin J. Stewart
(74) *Attorney, Agent, or Firm*—Shay Glenn LLP

(57) ABSTRACT

This invention is directed to a device and method of using the device for partitioning a patient's heart chamber into a productive portion and a non-productive portion. The device is particularly suitable for treating patients with congestive heart failure. The device has an inflatable partitioning element which separates the productive and non-productive portions of the heart chamber and in some embodiments also has a supporting element, which may also be inflatable, extending between the inflatable partitioning element and the wall of the non-productive portion of the patient's heart chamber. The supporting element may have a non-traumatic distal end to engage the ventricular wall or a tissue penetrating anchoring element to secure the device to the patient's heart wall.

9 Claims, 5 Drawing Sheets

U.S. PATENT DOCUMENTS

| | | |
|---|---|---|
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,578,069 A | 11/1996 | Miner, II |
| 5,634,936 A * | 6/1997 | Linden et al. ............... 606/213 |
| 5,634,942 A | 6/1997 | Chevillon et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,861,003 A * | 1/1999 | Latson et al. ............... 606/213 |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A * | 2/2000 | Huebsch et al. ............. 606/213 |
| 6,045,497 A | 4/2000 | Schweich et al. |
| 6,059,715 A | 5/2000 | Schweich et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,152,144 A * | 11/2000 | Lesh et al. .................. 128/898 |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 * | 1/2003 | Mazzocchi ................... 606/200 |
| 6,511,496 B1 | 1/2003 | Huter et al. |
| 6,537,198 B1 | 3/2003 | Vidlund et al. |
| 6,547,821 B1 * | 4/2003 | Taylor et al. ................. 623/3.1 |
| 6,551,303 B1 | 4/2003 | Van Tassel et al. |
| 6,592,608 B2 | 7/2003 | Fisher et al. |
| 6,652,555 B1 * | 11/2003 | VanTassel et al. ........... 606/200 |
| 6,685,627 B2 * | 2/2004 | Jayaraman ................... 600/37 |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,959,711 B2 * | 11/2005 | Murphy et al. .............. 128/898 |
| 6,994,093 B2 * | 2/2006 | Murphy et al. .............. 128/898 |
| 7,144,363 B2 | 12/2006 | Pai et al. |
| 7,320,665 B2 * | 1/2008 | Vijay .......................... 600/16 |
| 7,399,271 B2 * | 7/2008 | Khairkhahan et al. ......... 600/16 |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 * | 9/2002 | Murphy et al. ................ 623/3.1 |
| 2002/0161394 A1 * | 10/2002 | Macoviak et al. ............ 606/200 |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0045896 A1 * | 3/2003 | Murphy et al. .............. 606/191 |
| 2003/0050682 A1 | 3/2003 | Sharkey et al. |
| 2003/0050685 A1 | 3/2003 | Nikolic et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0181942 A1 | 9/2003 | Sutton et al. |
| 2003/0220667 A1 | 11/2003 | Van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0064014 A1 | 4/2004 | Melvin et al. |
| 2004/0127935 A1 | 7/2004 | VanTassel et al. |
| 2004/0172042 A1 | 9/2004 | Suon et al. |
| 2004/0260331 A1 * | 12/2004 | D'Aquanni et al. .......... 606/200 |
| 2004/0267378 A1 * | 12/2004 | Gazi et al. ................. 623/23.67 |
| 2005/0007031 A1 | 1/2005 | Hyder |
| 2005/0015109 A1 * | 1/2005 | Lichtenstein ................. 606/200 |
| 2005/0085826 A1 | 4/2005 | Nair et al. |
| 2005/0096498 A1 | 5/2005 | Houser et al. |
| 2005/0113861 A1 * | 5/2005 | Corcoran et al. ............. 606/200 |
| 2005/0154252 A1 | 7/2005 | Sharkey et al. |
| 2005/0177180 A1 | 8/2005 | Kaganov et al. |
| 2005/0216052 A1 * | 9/2005 | Mazzocchi et al. .......... 606/200 |
| 2005/0228434 A1 * | 10/2005 | Amplatz et al. .............. 606/200 |
| 2006/0014998 A1 * | 1/2006 | Sharkey et al. ................ 600/16 |
| 2006/0025800 A1 * | 2/2006 | Suresh ....................... 606/198 |
| 2006/0030881 A1 * | 2/2006 | Sharkey et al. .............. 606/213 |
| 2006/0229491 A1 | 10/2006 | Sharkey et al. |
| 2006/0264980 A1 * | 11/2006 | Khairkhahan et al. ....... 606/153 |
| 2006/0276684 A1 | 12/2006 | Speziali |
| 2006/0281965 A1 | 12/2006 | Khairkhahan et al. |
| 2007/0161846 A1 | 7/2007 | Nikolic et al. |
| 2007/0213578 A1 | 9/2007 | Khairkhahan et al. |
| 2007/0213815 A1 | 9/2007 | Khairkhahan et al. |
| 2008/0071298 A1 | 3/2008 | Khairkhahan et al. |
| 2008/0228805 A1 | 9/2008 | Bruck et al. |
| 2008/0293996 A1 | 11/2008 | Evans et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0187063 A1 | 7/2009 | Khairkhahan et al. |

| | | |
|---|---|---|
| 2009/0192539 A1* | 7/2009 | Lichtenstein ............... 606/191 |
| 2009/0254195 A1 | 10/2009 | Khairkhahan et al. |

FOREIGN PATENT DOCUMENTS

| WO | WO 01/30266 | 5/2001 |
|---|---|---|
| WO | WO 01/78625 A1 | 10/2001 |
| WO | WO 02/30335 | 4/2002 |
| WO | WO 02/071977 A2 | 9/2002 |
| WO | WO 03/007778 A | 1/2003 |
| WO | WO 03/073961 A1 | 9/2003 |
| WO | WO 2004/012629 A | 2/2004 |
| WO | WO 2004/047679 A1 | 6/2004 |
| WO | WO 2004/100803 | 11/2004 |
| WO | WO 2005/007031 | 1/2005 |

OTHER PUBLICATIONS

Vincent Dor, "The Treatment of Refractory Ischemic Ventricular Tachycardia by Endoventricular Patch Plasty Reconstruction of the Left Ventricle", Seminars in Thoracic and Cardiovascular Surgery, vol. 9, No. 2, pp. 146-155, Apr. 1997.

Daniel Giorgio Di Mattia et al., "Surgical treatment of left ventricular post-infarction aneurysm with endoventriculoplasty: late clinical and functional results", European Journal of Cardio-thoracic Surgery 15, pp. 413-419, 1999.

T Katsumata et al., "An objective appraisal of partial left ventriculectomy for heart failure", Journal of Congestive Heart Failure and Circulator Support, pp. 97-106, 1999.

Vincent Dor, "Surgery for left ventricular aneurysm", Current Opinion in Cardiology, Current Science, pp. 773-780, 1990.

Vincent Dor et al., "Ventricular remodeling in coronary artery disease", Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

International Search Report and Written Opinion for PCT/US2004/014782 mailed Sep. 21, 2004.

International Search Report and Written Opinion for PCT/US2005/000264 mailed Apr. 26, 2005.

Khairkhahan, et al., U.S. Appl. No. 10/436,959, entitled "System for improving cardiac function," filed May 12, 2003.

Khairkhahan, et al., U.S. Appl. No. 11/151,164, entitled "Peripheral seal for a ventricular partitioning device," filed Jun. 10, 2005.

Sharkey, et al., U.S. Appl. 11/199,633, entitled "Method for treating myocardial rupture," filed Aug. 9, 2005.

Khairkhahan et al; U.S. Appl. No. 11/860,438 entitled "Laminar ventricular partitioning device," filed Sep. 24, 2007.

Nikolic, et al., U.S. Appl. No. 12/129,443 entitled "Therapeutic methods and devices following myocardial infarction," filed May 29, 2008.

Khairkhahan et al; U.S. Appl. No. 12/125,015 entitled "Ventricular partitioning device," filed May 21, 2008.

Khairkhahan et al; U.S. Appl. No. 12/198,010 entitled "Retrievable devices for improving cardiac function," filed Aug. 25, 2008.

Khairkhahan, Alexander; U.S. Appl. No. 12/181,282 entitled "Inflatable ventricular partitioning device," filed Jul. 28, 2008.

Khairkhahan et al; U.S. Appl. No. 12/198,022 entitled "Retrievable cardiac devices," filed Aug. 25, 2008.

Khairkhahan et al; U.S. Appl. No. 12/268,346 entitled "System for improving cardiac function," filed Nov. 10, 2008.

Khairkhahan et al; U.S. Appl. No. 12/422,177 entitled "Sealing and filling ventricular partitioning devices to improve cardiac function," filed Apr. 10, 2009.

Khairkhahan et al; U.S. Appl. No. 12/422,144 entitled "System for improving cardiac function by sealing a partitioning membrane within a ventricle," filed Apr. 10, 2009.

Khairkhahan et al; U.S. Appl. No. 12/509,289 entitled "Peripheral seal for a ventricular partitioning device," filed Jul. 24, 2009.

U.S. Appl. No. 12/198,022.

U.S. Appl. No. 12/422,177.

Khairkhahan, et al; U.S. Appl. No. 11/801,075, entitled "System for improving cardiac function," filed May 7, 2007.

Khairkhahan at al; U. S. Appl. No. 11/800,998, entitled "System for improving cardiac function," filed May 7, 2007.

Nikolic et al; U.S. Appl. No. 11/640,469, entitled "Cardiac device and methods of use thereof," filed Dec. 14, 2006.

* cited by examiner

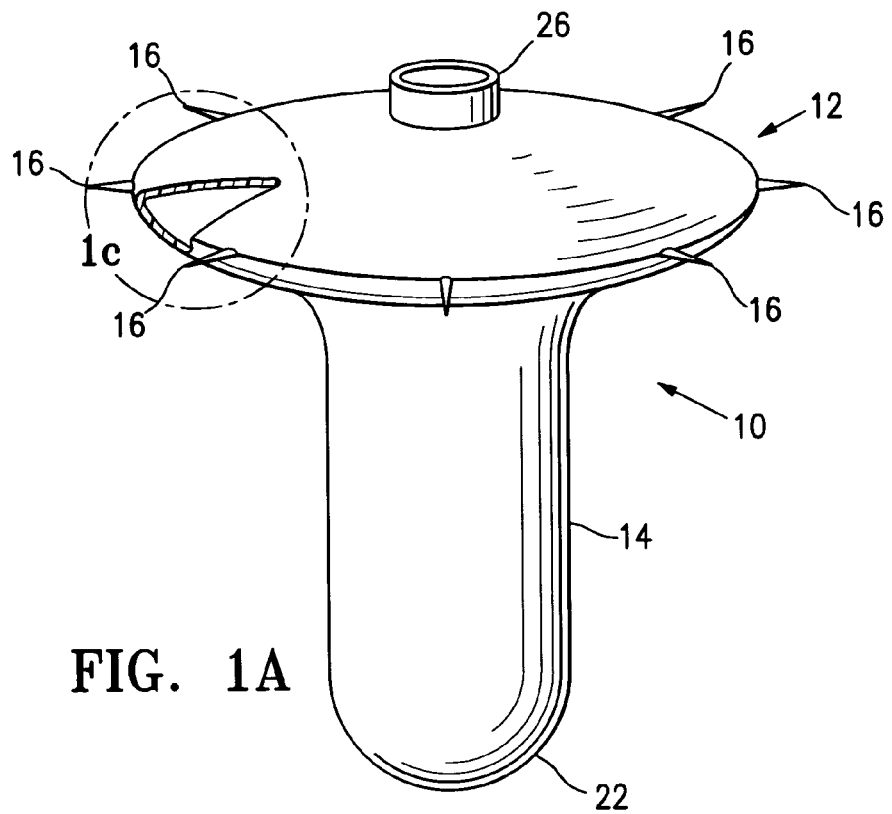
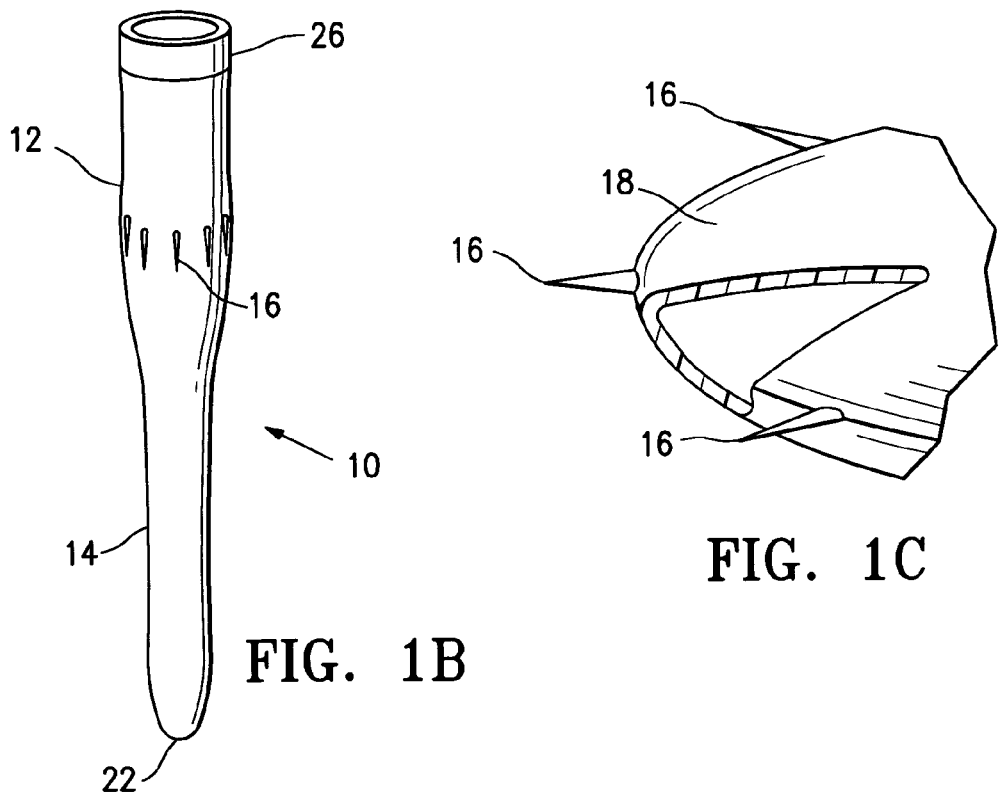
FIG. 1A
FIG. 1B
FIG. 1C

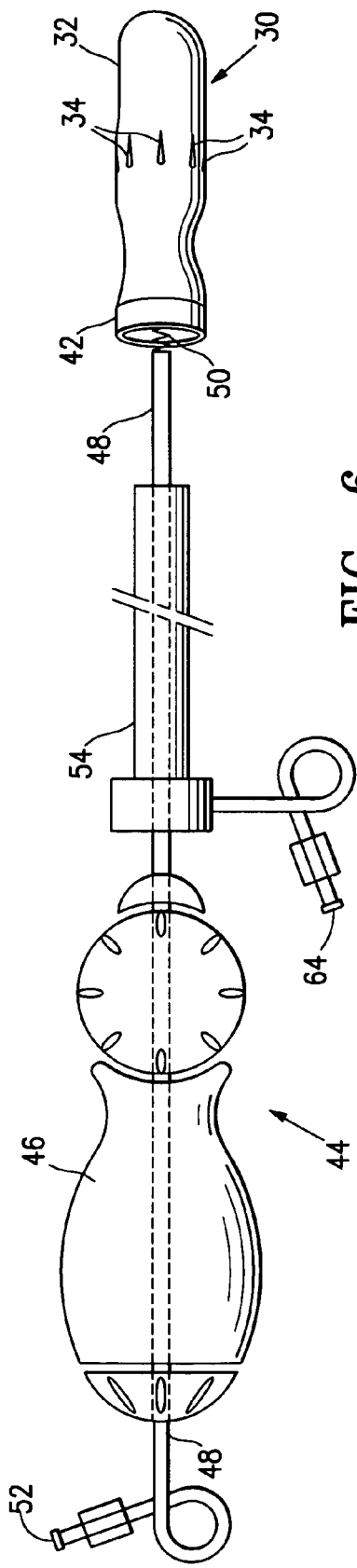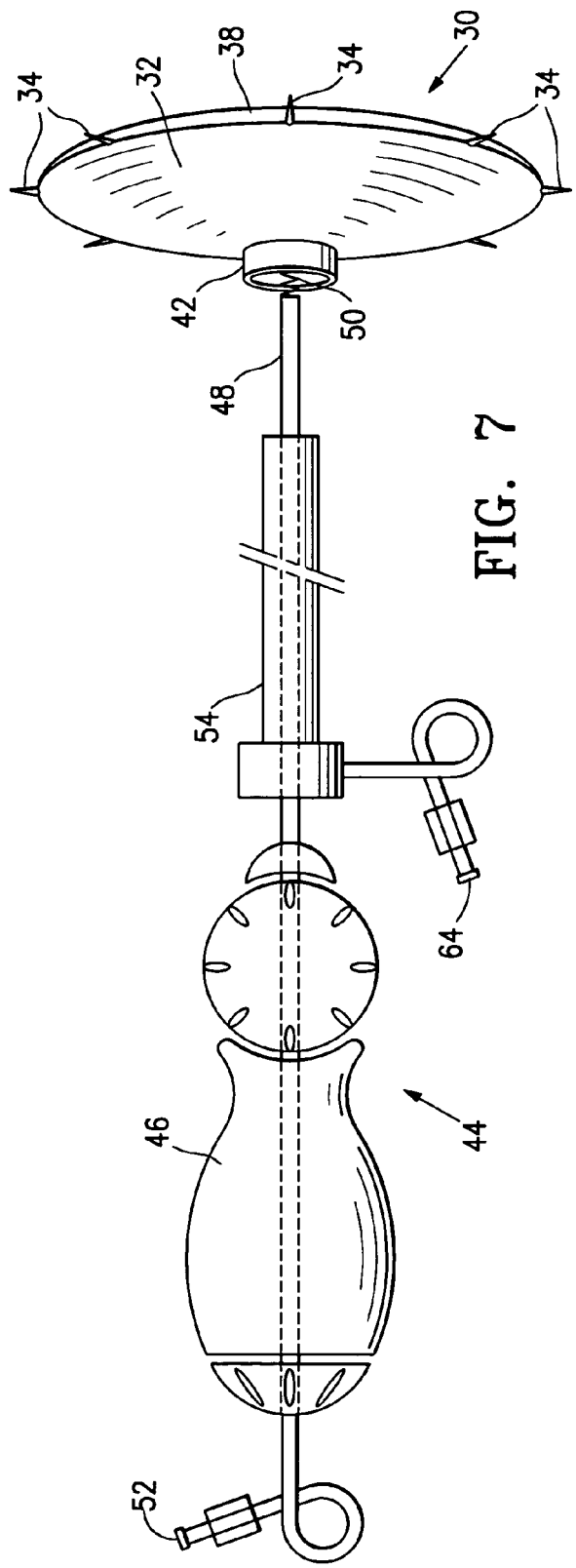

INFLATABLE VENTRICULAR PARTITIONING DEVICE

FIELD OF THE INVENTION

The present invention relates generally to the field of treating congestive heart failure and more specifically, to a device and method for partitioning a patient's heart chamber and a system for delivering the treatment device.

BACKGROUND OF THE INVENTION

Congestive heart failure (CHF) is characterized by a progressive enlargement of the heart, particularly the left ventricle and is a major cause of death and disability in the United States. Approximately 500,000 cases occur annually in the U.S. alone. As the patient's heart enlarges, it cannot efficiently pump blood forward with each heart beat. In time, the heart becomes so enlarged the heart cannot adequately supply blood to the body. Even in healthy hearts only a certain percentage of the blood in a patient's left ventricle is pumped out or ejected from the chamber during each stroke of the heart. The pumped percentage, commonly referred to as the "ejection fraction", is typically about sixty percent for a healthy heart. A patient with congestive heart failure can have an ejection fraction of less than 40% and sometimes lower. As a result of the low ejection fraction, a patient with congestive heart failure is fatigued, unable to perform even simple tasks requiring exertion and experiences pain and discomfort. Further, as the heart enlarges, the internal heart valves such as the mitral valve, cannot adequately close. An incompetent mitral valve allows regurgitation of blood from the left ventricle back into the left atrium, further reducing the heart's ability to pump blood forewardly.

Congestive heart failure can result from a variety of conditions, including viral infections, incompetent heart valves (e.g. mitral valve), ischemic conditions in the heart wall or a combination of these conditions. Prolonged ischemia and occlusion of coronary arteries can result in myocardial tissue in the ventricular wall dying and becoming scar tissue. Once the myocardial tissue dies, it is less contractile (sometimes non-contractile) and no longer contributes to the pumping action of the heart. It is referred to as hypokinetic. As the disease progresses, a local area of compromised myocardium may bulge out during the heart contractions, further decreasing the heart's ability to pump blood and further reducing the ejection fraction. In this instance, the heart wall is referred to as dyskinetic or akinetic. The dyskinetic region of the heart wall may stretch and eventually form an aneurysmic bulge.

Patients suffering from congestive heart failure are commonly grouped into four classes, Classes I, II, III and IV. In the early stages, Classes I and II, drug therapy is presently the most commonly prescribed treatment. Drug therapy typically treats the symptoms of the disease and may slow the progression of the disease, but it can not cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, Furthermore, there are not enough hearts available for transplant to meet the needs of CHF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually limited to Class IV patients and, accordingly, is not an option for patients facing ineffective drug treatment prior to Class IV. Finally, if the procedure fails, emergency heart transplant is the only presently available option.

Other efforts to treat CHF include the use of an elastic support, such as an artificial elastic sock placed around the heart to prevent further deleterious remodeling.

Additionally, mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Recently, improvements have been made in treating patient's with CHF by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta. While this procedure has been found to be successful in providing some relief from CHF symptoms and slowed the progression of the disease, it has not been able to stop the disease.

SUMMARY OF INVENTION

The present invention is directed to a ventricular partitioning device and method of employing the device in the treatment of a patient with congestive heart failure. Specifically, the ventricular chamber of the CHF patient is partitioned by the device so as to reduce its total volume and to reduce the stress applied to the heart and, as a result, improve the ejection fraction thereof.

A ventricular partitioning device embodying features of the invention has an inflatable partitioning element, which is configured to partition the patient's ventricular heart chamber into a main productive portion and a secondary non-productive portion. The inflatable partitioning element may be at least in part disc shaped and hollow. The partitioning device preferably has a supporting or spacing element extending from the distal side of the inflatable partitioning element for non-traumatically engaging a region of the patient's ventricular wall defining in part the secondary non-productive portion to space a central portion of the partitioning element from the heart wall. The supporting or spacing element may itself be inflatable and preferably has an interior in fluid communication with the interior of the partitioning element.

The supporting element of the device has a length configured to extend to the heart wall, supporting and spacing the partitioning element from the heart wall. The supporting element may have an inner lumen extending therein for delivery of therapeutic or diagnostic agents through the ports provided along the length thereof.

The partitioning device may be delivered percutaneously or intraoperatively. It is relatively easy to install and provides substantial improvement in the ejection fraction of the patient's heart chamber. A suitable delivery system is described in co pending application Ser. No. 10/212,032, filed on Aug. 1, 2002 which is incorporated herein in it's entirety. These and other advantages of the invention will become more apparent from the following detailed description of the invention and the accompanying exemplary drawings.

BRIEF DESCRIPTION OF THE DRAWINGS

FIG. 1A is a perspective view of a ventricular partitioning device in an inflated state embodying features of the invention.

FIG. 1B is a perspective view of a ventricular portioning device in a deflated state embodying features of the invention.

FIG. 1C is an enlarged view of the encircled region of FIG. 1A.

FIG. 6 is an elevational view of a delivery system for the partitioning device shown in FIG. 3 with the inflatable partitioning element in a deflated condition.

FIG. 7 is an elevational view of a delivery system as shown in FIG. 6 with the partitioning element in an inflated condition.

DETAILED DESCRIPTION OF EMBODIMENTS OF THE INVENTION

Figure 2:
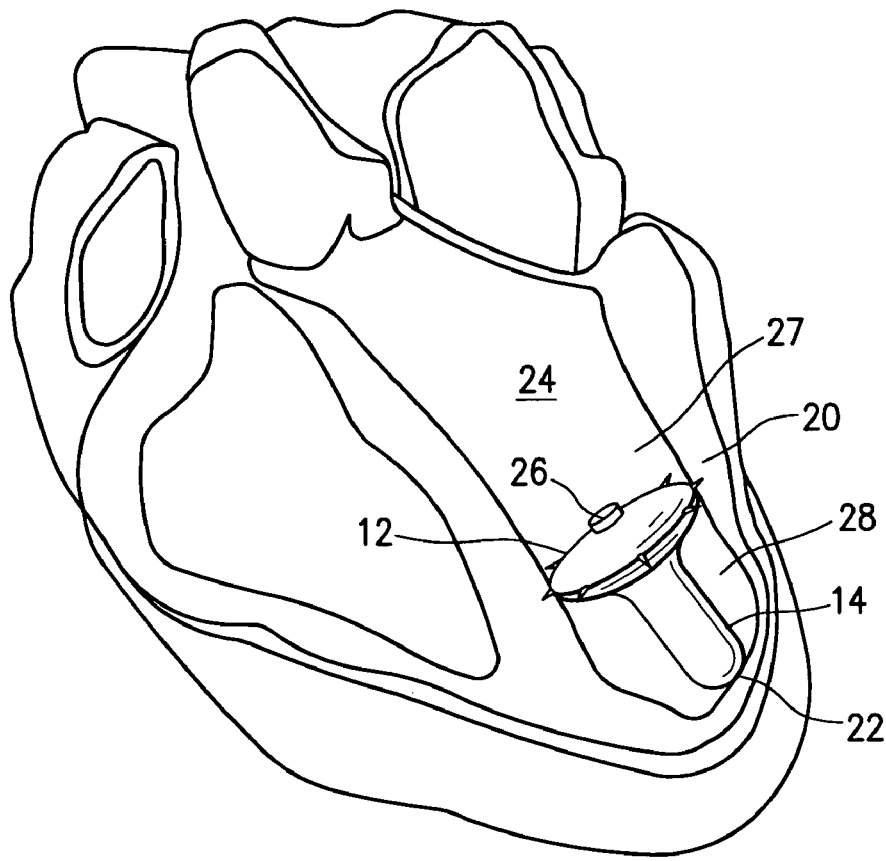
FIG. 2 is a schematic view of a patient's left ventricular chamber illustrating the partitioning device shown in FIG. 1A disposed within the chamber separating a working portion of the chamber from a non-working portion of the chamber.

FIGS. 1A and 1B illustrate a partitioning device 10 which embodies features of the invention and which includes an inflatable partitioning element 12 and an inflatable supporting element 14. The partitioning element 12 may contain anchoring members 16 around its edge 18 to engage the heart wall 20 upon expansion. The partitioning device 10 is delivered in a deflated form through a catheter. The inflatable partitioning element may be disc shaped and hollow. When inflated the supporting element 14 extends distally from the center of the partitioning element 12 and has a distal end 22 which provides a yielding engagement with a heart wall 20 when deployed within a patient's heart chamber 24.

The partitioning element 12 has a peripheral edge 18. The edge 18 may contain anchoring members 16 which are configured to hold the partitioning device 10 in a deployed position within the patient's heart chamber 24. Preferably, the anchoring elements 16 penetrate into tissue of the patient's heart wall 20 in order to secure the partitioning element 12 so as to partition the ventricular chamber 24 in a desired manner. The partitioning element 12 may contain a hub 26 having a one way valve for inflation of both the partitioning element 12 and the supporting element 14.

FIG. 2 illustrates the placement of partitioning device 10 within a patient's left ventricle 24. The partitioning element 12 partitions the patient's heart chamber 24 into a main productive portion 27 and a secondary, essentially non-productive portion 28. The productive portion 27 is smaller than the original ventricular chamber 24 and provides for an improved ejection fraction. The partitioning increases the ejection fraction and provides an improvement in blood flow through the heart chamber. Over time, the non-productive portion 28 fills initially with thrombus and subsequently cellular growth. Bio-resorbable fillers such as polylactic acid, polyglycolic acid, polycaprolactone and copolymers and blends may be employed to fill the non-productive portion 28. Fillers may be suitably supplied in a suitable solvent such as DMSO. Other materials which accelerate tissue growth may be deployed in the non-productive portion 28. In some embodiments the supporting element 14 may fill a portion or all of the non-productive chamber 28.

Figure 3:
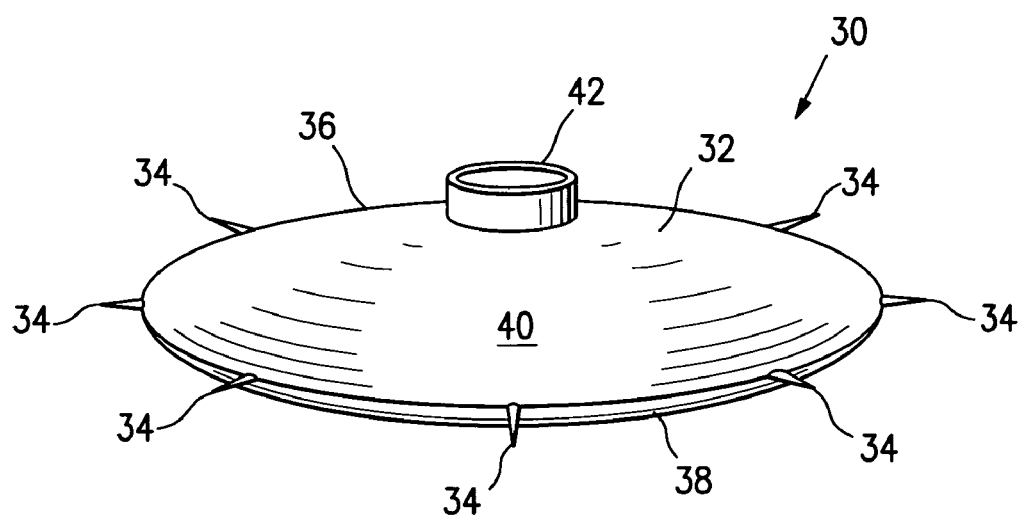
FIG. 3 is a perspective view of an alternative design of the partitioning device without a supporting member.

An alternative partitioning device 30 is shown in FIG. 3 wherein the inflatable partitioning element 32 is held in place by anchoring members 34 disposed about the periphery 36. In this embodiment the partitioning element 32 does not have a distal supporting element extending from it's distal face 38. The proximal face 40 has a hub 42 which has a inflation port for injection inflation fluid into the interior of the element 32.

Figure 4:
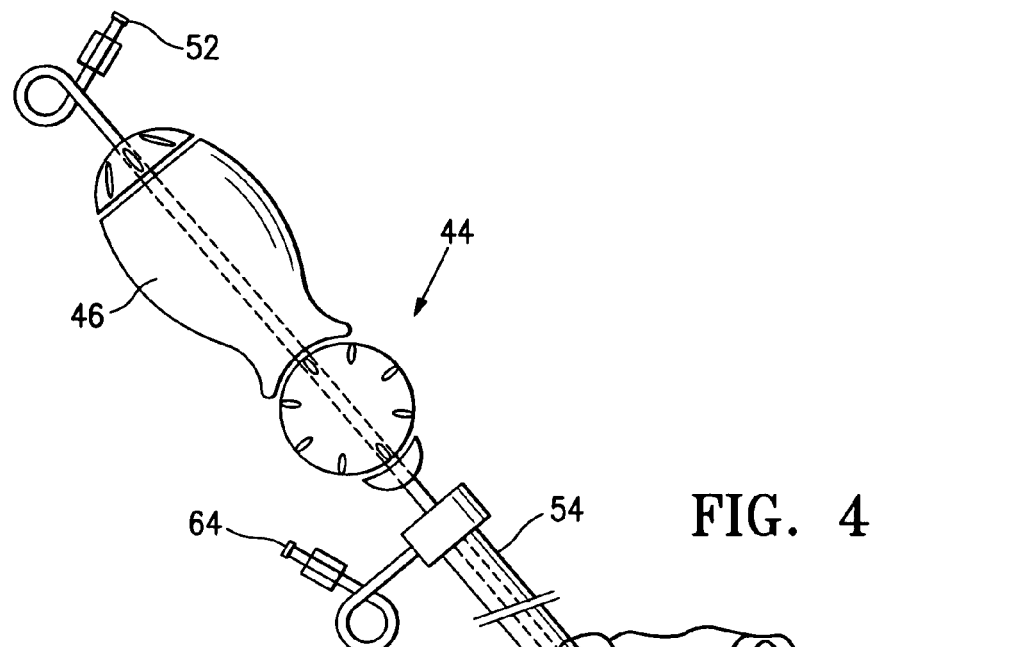
FIG. 4 is a schematic view of a patient's left ventricular chamber illustrating the partitioning device being deployed on a delivery system.

A suitable delivery system for the partitioning devices described above is described in co-pending application Ser. No. 10/212,032 filed on Aug. 1, 2002 which is incorporated herein in its entirety. FIGS. 4, 6 and 7 illustrate a suitable delivery system 44 with a partitioning device 30 as shown in FIG. 3. The delivery system 44 includes a control handle 46 with a delivery catheter 48 and a detachment mechanism including coil 50 secured to the distal end of the delivery catheter for releasing the partitioning device 30 from the delivery system 44 The delivery catheter 48 may be provided with an inner lumen (not shown) through which therapeutic or diagnostic fluids may be delivered. The delivery catheter 48 extends through the handle 46 and the proximal end of the catheter 48 is connected to a balloon inflation port 52.

Figure 5:
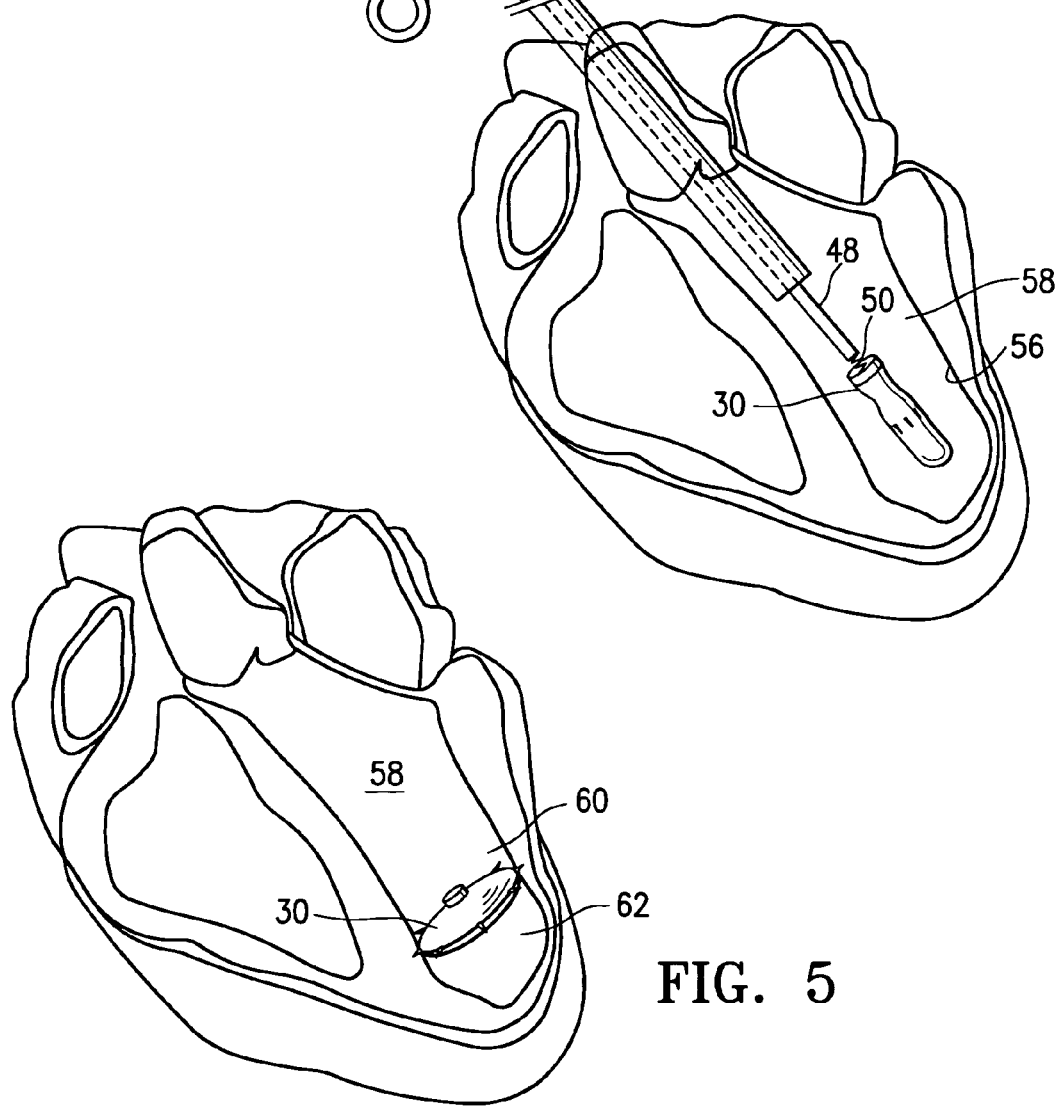
FIG. 5 is a schematic view of the patient's left ventricular chamber illustrating the partitioning device Shown in FIG. 3 disposed within the chamber separating a working portion of the chamber from a non-working portion of the chamber.

As shown in FIG. 4, the delivery system 44 may be introduced into a patient's body through a percutaneously introduced guide catheter or cannula 54 which has an inner lumen (not shown). The partitioning device 30 is slidably disposed within the inner lumen of guide catheter 54. The delivery system 44 is advanced distally within the inner lumen of the guide catheter 54 and engages the ventricular wall 56. With the delivery system 44 held in place, the partitioning element 32 is inflated and the anchoring members 34 penetrate into tissue of the patient's heart wall 56, as shown in FIG. 5, to secure the partitioning device 30 within the patient's heart chamber 58 to partition the chamber into productive portion 60 and non-productive portion 62. The delivery system 44 and the guide catheter 54 may then be removed from the patient. The proximal end of the guide catheter 54 is provided with an injection port 64 to inject therapeutic or diagnostic fluids through the inner lumen thereof into the patient's heart chamber 58.

Figure 8:
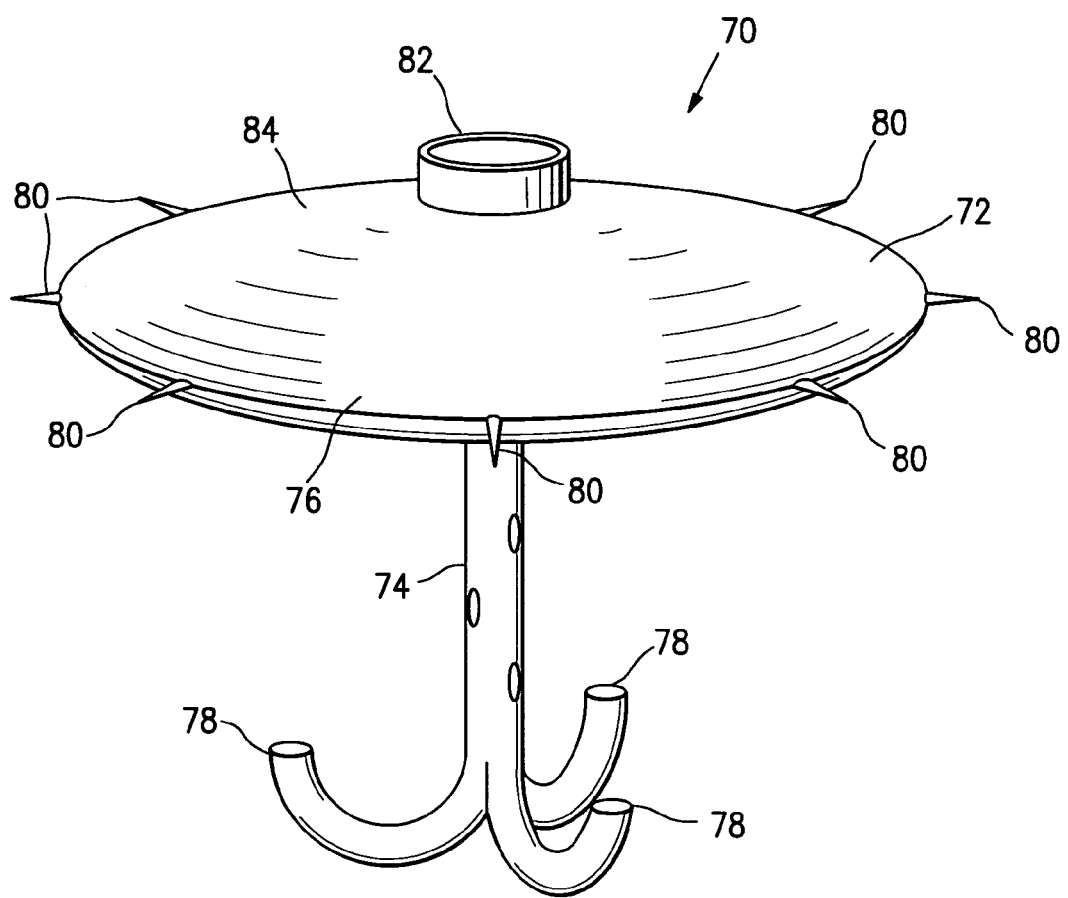
FIG. 8 is a perspective view of an alternative partitioning device which has an elongated, distally extending stem with non-traumatic bumper elements on the distal extremity.

FIG. 8 illustrates another alternative inflatable partitioning device 70 which has a partitioning element 72 and a stem 74 which extends distally from the distal face 76 of the partitioning element. The distal extremity of the stem 74 has three J-shaped bumpers 78 which allow for non-traumatic engagement with the wall of the patient's non-productive portion of the heart chamber. A variety of other non-traumatic bumpers may be employed, such as those described in co-pending application Ser. No. 10/754,182, which was filed on Jan. 9, 2004 and which was entitled "VENTRICULAR PARTITIONING DEVICE". This application has been assigned to the present assignee and is incorporated herein in its entirety. The periphery of partitioning element 72 is provided with a plurality of anchoring elements 80 for securing the device to the ventricular wall. A hub 82 is provided on the proximal face 84 of the partitioning element 72 for delivery and inflation of the partitioning element as previously described.

To assist in properly locating the partitioning device during advancement and placement thereof into a patient's heart chamber, it may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

The partitioning device 10, 30 and 70 may be formed of suitable biocompatitble polymeric material which include expanded polytetrfluoroethylene (ePTFE), polyethylene terephthalate (PET), polyesters such as Hytrel®, polyamides such as Nylon and polyurethane. The compliance may range from about 50 to about 1000%. The inflatable partitioning element of the device in the expanded configuration has radial dimensions from about 5 to about 60 mm, preferably about 20 to about 50 mm, as measured from the center line axis. The aspect ratio of the thickness of the inflatable partitioning element at its thickest portion to the diameter of the inflatable partitioning element is from about 1:10 to about 1:1, preferably about 1:10 to about 1:2.

The delivery catheter and the guide catheter may be formed of suitable high strength polymeric material such as PEEK (polyetheretherketone), polycarbonate, PET, Nylon, and the like. To the extent not otherwise described herein, the various components of the partitioning device and delivery system may be formed of conventional materials and in a conventional manner as will be appreciated by those skilled in the art.

The inflatable partitioning and support elements may be inflated with a variety of fluids, preferably liquids such as saline or contrast fluids. Liquids which become more viscous or harden in situ may also be used. If the inflatable elements are formed of bioabsorable materials, the inflation fluid should be readily absorbed within the patient's bloodstream and should not have significant detrimental affects.

While particular forms of the invention have been illustrated and described herein, it will be apparent that various modifications and improvements can be made to the invention. For example an inflatable partitioning element may be used to occlude an atrial appendage of the heart. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element", "member", "device", "section", "portion", "steps", "means" and words of similar import when used herein shall not be construed as invoking the provisions of 35 U.S.C. §112(6) unless the following claims expressly use the terms "means" followed by a particular function without specific structure or "step" followed by a particular function without specific action. All patents and patent applications referred to above are hereby incorporated by reference in their entirety. Accordingly, it is not intended that the invention be limited, except as by the appended claims.

What is claimed is:

1. A method of treating a patient with congestive heart failure, comprising:

providing a device comprising an inflatable partitioning element with a peripheral edge having at least one hook or barb anchoring element extending from the peripheral edge;

positioning the device within a ventricular chamber of the patient's heart;

inflating an interior of the inflatable partitioning element with an inflation fluid;

anchoring the peripheral edge of the inflatable partitioning element to a wall of the ventricular chamber to secure the device to the wall of the ventricular chamber and to partition the chamber into a productive chamber and a non-productive chamber so that the peripheral edge separates the productive and non-productive chambers; and spacing a distal face of the inflatable partitioning element from a region of a ventricular wall defining at least in part the non-productive ventricular chamber.

2. The method of claim 1 wherein the device further comprises a distal extending support element which spaces the partitioning element.

3. The method of claim 1 further comprising delivering the inflatable partitioning element in a deflated configuration and expanding the inflatable partitioning element within the patient's heart.

4. The method of claim 1 further comprising positioning the device within an inner lumen of an elongated catheter, percutaneously introducing the catheter into the patient's vasculature, and advancing the device therein to the patient's heart wherein the device is discharged from the catheter.

5. The method of claim 1 wherein the inflating step comprises introducing an inflation fluid other than blood into an interior portion of the inflatable partitioning element.

6. A method of treating a patient with congestive heart failure, comprising the steps of:

a. providing a treatment device having an inflatable partitioning element with a peripheral edge having at least one hooked or barbed anchoring element extending from the peripheral edge;

b. providing an inflatable supporting element extending distally from the inflatable partitioning element;

c. positioning the treatment device within a ventricular chamber of the patient's heart;

d. inflating an interior of the inflatable partitioning element with an inflation fluid;

e. anchoring the peripheral edge of the partitioning element to secure the device to the wall of the ventricular chamber and to partition the chamber into a productive chamber and a non-productive chamber so that the peripheral edge separates the productive and non-productive chambers; and f. spacing a distal face of the inflatable partitioning element from a region of a ventricular wall defining at least in part the non-productive ventricular chamber.

7. The method of claim 6, wherein the step of positioning the device within the ventricular chamber comprises extending the supporting element from the distal face of the inflatable partitioning element to separate the distal face of the inflatable partitioning element from the wall of the ventricular chamber.

8. A method of treating a patient with congestive heart failure, comprising:
   positioning the an inflatable device within a ventricular chamber of the patient's heart;
   inflating an interior of an inflatable partitioning element of the inflatable device with an inflation fluid, wherein the inflatable partitioning element comprises at least one hook or barb anchoring element extending from the peripheral edge;
   engaging and anchoring the peripheral edge of the inflatable partitioning element with a wall of the ventricular chamber to partition the chamber into productive and non-productive chambers so that the peripheral edge separates the productive and non-productive chambers; and
   spacing a distal face of the inflatable partitioning element from a region of a ventricular wall defining at least in part the non-productive ventricular chamber.

9. The method of claim 1 or 8, wherein the step of positioning the device within the ventricular chamber comprises extending a supporting element from the distal face of the inflatable partitioning element to separate the distal face of the inflatable partitioning element from the wall of the ventricular chamber.

* * * * *